(12) United States Patent
Trygstad et al.

(10) Patent No.: US 9,476,847 B2
(45) Date of Patent: *Oct. 25, 2016

(54) SPECTROSCOPIC CRUDE OIL ANALYSIS

(71) Applicant: Invensys Systems, Inc., Foxboro, MA (US)

(72) Inventors: W. Marcus Trygstad, Spring, TX (US); Russell Jackson, Sudbury, MA (US); Bruce A. Keen, Bartlesville, OK (US)

(73) Assignee: Invensys Systems, Inc., Foxboro, MA (US)

( * ) Notice: Subject to any disclaimer, the term of this patent is extended or adjusted under 35 U.S.C. 154(b) by 741 days.

This patent is subject to a terminal disclaimer.

(21) Appl. No.: 13/914,137

(22) Filed: Jun. 10, 2013

(65) Prior Publication Data

US 2013/0342203 A1 Dec. 26, 2013

Related U.S. Application Data

(63) Continuation-in-part of application No. 12/624,041, filed on Nov. 23, 2009, now Pat. No. 8,497,683, which is a continuation-in-part of application No. 11/866,214, filed on Oct. 2, 2007, now Pat. No. 7,667,461.

(60) Provisional application No. 60/848,936, filed on Oct. 3, 2006.

(51) Int. Cl.
*G01N 24/08* (2006.01)
*G01R 33/31* (2006.01)
(Continued)

(52) U.S. Cl.
CPC ............ *G01N 24/08* (2013.01); *G01R 33/307* (2013.01); *G01R 33/31* (2013.01); *G01N 21/35* (2013.01); *G01N 21/359* (2013.01); *G01N 21/65* (2013.01); *G01N 24/081* (2013.01); *G01N 24/085* (2013.01)

(58) Field of Classification Search
USPC ............... 324/300–322; 600/407–435; 382/128–131
See application file for complete search history.

(56) References Cited

U.S. PATENT DOCUMENTS 3,061,723 A * 10/1962 Kapff ............... G01N 21/64
250/301
3,087,888 A * 4/1963 Saraceno ............ C10G 11/00
196/132

(Continued)

OTHER PUBLICATIONS

Watlow, Cast-X Series 2000 Circulation Heaters, 2005 Watlow Electric Manufacturing Company, 4pgs Publication date is not available.

(Continued)

*Primary Examiner* — Melissa Koval
*Assistant Examiner* — Tiffany Fetzner
(74) *Attorney, Agent, or Firm* — Stephen Manetta; Ralph Graham

(57) ABSTRACT

A spectroscopic sample analysis apparatus includes an actively controlled heat exchanger in serial fluid communication with a spectroscopic analyzer, and a controller communicably coupled to the heat exchanger. The heat exchanger is disposed downstream of a fluid handler in the form of a stream selection unit/stream switching unit (SSU), a solvent/standard recirculation unit (SRU), and/or an autosampling unit (ASU). The SSU selectively couples individual stream inputs to an output port. The SRU includes a solvent/standard reservoir, and selectively couples output ports to the heat exchanger, and returns the solvent/standard sample to the reservoirs. The ASU includes a sample reservoir having a sample transfer pathway with a plurality of orifices disposed at spaced locations along a length thereof. The controller selectively actuates the fluid handler, enabling sample to flow there through to the heat exchanger, and actuates the heat exchanger to maintain the sample at a predetermined temperature.

14 Claims, 8 Drawing Sheets

(51) Int. Cl.
*G01N 21/35* (2014.01)
*G01N 21/359* (2014.01)
*G01N 21/65* (2006.01)
*G01R 33/30* (2006.01)

(56) References Cited

U.S. PATENT DOCUMENTS

| | | | |
|---|---|---|---|
| 3,480,416 A * | 11/1969 | Bitterlich | C10G 11/00 422/201 |
| 5,132,225 A * | 7/1992 | Dickakian | G01N 30/90 208/309 |
| 6,380,737 B1 | 4/2002 | Myles | |
| 6,528,018 B1 | 3/2003 | Berndt | |
| 6,544,799 B1 | 4/2003 | Lewis et al. | |
| 6,795,780 B1 | 9/2004 | Hyde | |
| 7,217,360 B2 | 5/2007 | Brann | |
| 7,667,461 B2 * | 2/2010 | Trygstad | G01N 24/08 324/315 |
| 8,497,683 B2 * | 7/2013 | Trygstad | G01N 24/08 324/315 |
| 2005/0013740 A1 * | 1/2005 | Mason | G01N 21/79 422/68.1 |
| 2008/0058697 A1 | 3/2008 | Kamen et al. | |
| 2008/0211505 A1 * | 9/2008 | Trygstad | G01N 24/08 324/321 |
| 2010/0066374 A1 * | 3/2010 | Trygstad | G01N 24/08 324/321 |
| 2013/0342203 A1 * | 12/2013 | Trygstad | G01R 33/307 324/309 |

OTHER PUBLICATIONS

Product Brochure, Product Platform: Circulation Heaters, Watlow's CAST-X Family of Heaters, p. 7, Publication date is not available.

* cited by examiner

FIG. 3

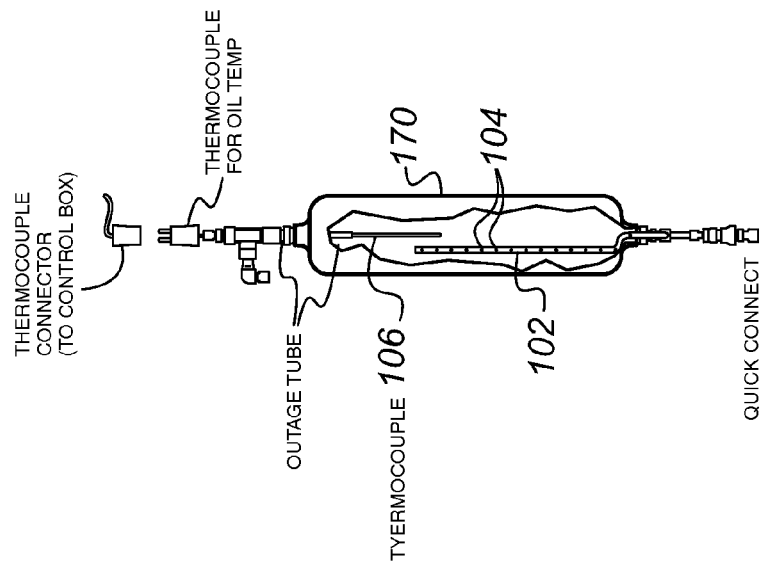
FIG. 7
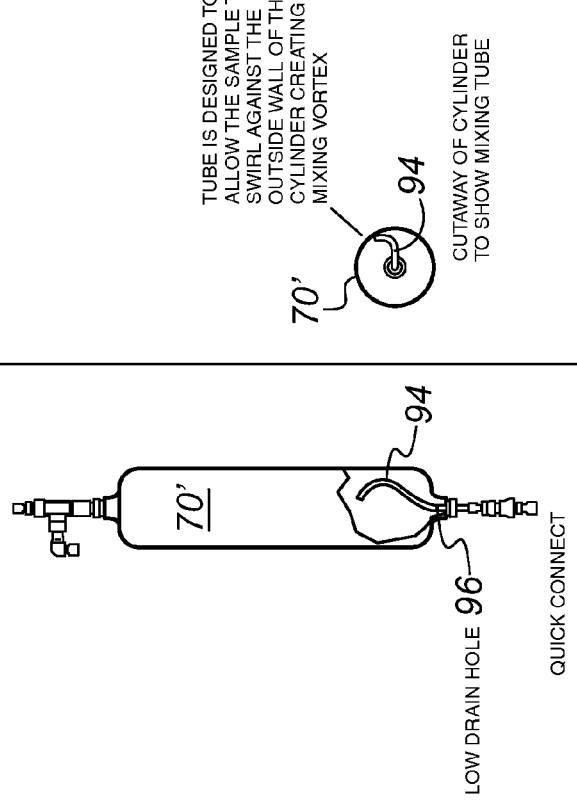
FIG. 6
FIG. 5

SPECTROSCOPIC CRUDE OIL ANALYSIS

RELATED APPLICATION

This application is a Continuation of U.S. Pat. No. 8,497,683, entitled SPECTROSCOPIC SAMPLE ANALYZER AND SAMPLE HANDLING SYSTEM, issued Jul. 30, 2013, which is a Continuation-In-Part of U.S. Pat. No. 7,667,461, entitled Sample Analyzer and Sampling System, issued Feb. 23, 2010, and which claims the benefit of U.S. Provisional Application Ser. No. 60/848,936, entitled Sample Analyzer and Sampling System, filed on Oct. 3, 2006, the contents of which are incorporated herein by reference in their entirety for all purposes.

BACKGROUND

1. Technical Field

This invention relates to the measurement of chemical and physical properties of flowing streams of liquids, solids or mixed liquids and solids by quantitative nuclear magnetic resonance (NMR) spectroscopy, but may be applied to other types of molecular spectroscopy including infrared (IR), near-infrared (NIR), and Raman spectroscopy. In particular, this invention relates to sample analyzers and systems for managing sample introduction into the analyzers.

2. Background Information

The analysis of materials using NMR requires a region of space containing a magnetic field that is either extremely uniform in magnetic flux density or else extremely uniform in the spatial gradient of magnetic flux density. In such a region, a sample to be analyzed is subjected to a short pulse of electromagnetic energy at a predetermined frequency that is a function of the atomic nuclei to be analyzed and of their chemical bonding. The pulse is coupled to the sample by a surface coil. A typical pulse duration is of the order of fifty microseconds, although the pulse width that is chosen is a function of the characteristic relaxation time of the subject nuclei in material being analyzed. The magnetic field causes the magnetic moments of the constituent nuclei in the sample to become aligned along lines of magnetic flux. If the field is strong and uniform to a relatively high degree of precision, the magnetic moments will be essentially parallel to each other, resulting in an aggregate or bulk magnetic moment. The electromagnetic energy coupled to the sample effects a change in the bulk magnetic moment. The relaxation of the bulk magnetic moment from the re-aligned position back to the original position when the pulse is ended produces signals that may be detected and transformed into a spectrum, in which response intensity plotted as a function of frequency is unique to the particular sample composition. Due to the temperature dependence of both the consistency of the magnetic field and a sample's spectral behavior, temperature control of both within appropriate tolerances is desired.

NMR spectrometers came into use in the research laboratory in the early 1960s. As NMR technology advanced, it became a ubiquitous tool for elucidating molecular structure, chemical behavior and reaction mechanisms, and molecular level interactions in biological systems and diverse organic molecules including pharmaceuticals and polymers. Generally such investigations are performed on pure materials or carefully controlled mixtures to permit observation of the chemical phenomenon of interest. Understanding about the chemistry may be deduced through examination by a skilled spectroscopist of features in a single spectrum or a series of spectra measured on the subject chemical system under limited number of experimentally controlled conditions.

More recently, NMR analysis has also been used in various production environments to analyze flowing liquids, pastes, slurries, or solids in powdered or other finely divided form. NMR analyzers may be used to perform in minutes the measurement of multiple chemical and physical properties, which otherwise would need to be analyzed by many different analytical methods in a quality control laboratory, requiring hours or even days. This capability to perform multiple analyses with high frequency automatically, makes process NMR analysis a cost-effective means for characterizing input and output streams associated with diverse chemical processes. A typical NMR analyzer commonly used for such process applications includes the D-Mash NMR analyzer available from The Qualion Company, Haifa Israel.

Process streams that may be difficult to analyze continuously by means other than NMR include those which have high optical density, high loading of fine particulates or solids, high water content, or relatively high viscosity. Exemplary applications therefore may include those in oil and petrochemical processing plants, chemical plants, and other industries requiring automatic process control of fluids. In the petrochemical field, these analyzers have been used in crude blending, fast CDU optimization after crude feed switching, effective feed control and optimization of FCC (Fluid Catalytic Cracking) unit applications. Other industries that may benefit from NMR analyzers include plastics and polymers, pharmaceuticals, food and beverages.

In contrast to traditional use of analytical NMR spectroscopy in research applications, petrochemical streams can contain dozens or hundreds of compounds. Accordingly, the objective is no longer structural elucidation or detailed chemical characterization, but the measurement of bulk properties such as distillation yields at various temperatures, the total aromatic content, acidity, bulk sulfur content, octane in gasoline, cetane in diesel, and cloud point in jet fuel. Also, the analysis of a sample spectrum to obtain property values is performed automatically by software, which applies property-specific models based on data sets of dozens or hundreds of calibration samples whose spectra were measured previously and corresponding property values analyzed in the laboratory.

It follows that the quality of property models depends at a minimum on the compositional diversity of the calibration sample set and the precise measurement of NMR spectra. The latter requires proper tuning of the NMR spectrometer to achieve a magnetic field of suitable uniformity and the supply to it of samples maintained at relatively uniform temperature. For example, even relatively slight variations in sample temperature, e.g., variations as small as plus or minus 3 degrees C., may significantly reduce measurement accuracy. A set of calibration samples whose compositional diversity is suitable for creation of property models may be obtained most conveniently by collecting and storing samples over a relatively long time frame during which feed or product streams associated with a process exhibit relevant property variations.

A need therefore exists for an apparatus and method for maintaining and supplying samples to an NMR analyzer in a relatively uniform state, both on-line within a process, and off-line in a batch processing mode.

SUMMARY

One aspect of the present invention includes an apparatus for sample analysis. The apparatus includes an actively controlled heat exchanger configured for upstream serial fluid communication with a magnetic resonance analyzer, and a controller communicably coupled to the heat exchanger. The heat exchanger is placed downstream of at least one fluid handler. The fluid handler is selected from the group consisting of a stream selection unit (SSU), a solvent/standard recirculation unit (SRU), and an auto-sampling unit (ASU).

The SSU includes a plurality of stream input ports, a stream output port, and one or more SSU valves configured to selectively couple individual ones of the stream input ports to the stream output port. The controller is configured to selectively actuate the SSU valves to select and couple a stream source to the stream output port, and actuate the heat exchanger to maintain a sample of the stream source at a predetermined temperature.

The SRU includes one or more solvent/standard reservoirs, a fluid output port associated with each of the reservoirs, and one or more SRU valves coupled to the output ports, to selectively couple an individual one of the fluid output ports to the heat exchanger. The controller is configured to selectively actuate individual ones of the SRU valves to couple a reservoir to the heat exchanger, and to actuate the heat exchanger to maintain a sample of solvent/standard at a predetermined temperature for input into the analyzer. A return line is configured to return the solvent/standard sample to the reservoirs from the analyzer.

The ASU includes one or more sample reservoirs configured to store samples therein, and a sample port respectively coupled to each of the reservoirs. The sample reservoirs each have a sample transfer pathway coupled to the sample port and extending into the reservoir, the pathway having a plurality of orifices disposed at spaced locations along a length thereof. One or more ASU valves selectively couple the sample port to the heat exchanger. The controller is configured to selectively actuate the ASU valves to enable a sample to flow through the sample pathway to the heat exchanger, and to actuate the heat exchanger to maintain the sample at a predetermined temperature.

In another aspect of the invention, a sample handling apparatus includes a stream selection unit (SSU). The SSU includes a plurality of stream input ports, a stream output port, and one or more SSU valves configured to selectively couple individual stream input ports to the stream output port. A pump is disposed in serial fluid communication with the stream output port, and an actively controlled heat exchanger is located in series with the stream output port. A controller is configured to selectively actuate the pump and the SSU valves to select and couple a stream source to the stream output port, and actuate the heat exchanger to maintain a sample of the stream source at a predetermined temperature for input to a magnetic resonance analyzer.

In still another aspect of the invention, a sample handling apparatus includes a solvent/standard recirculation unit (SRU). The SRU includes one or more solvent/standard reservoirs, a fluid output port respectively associated with each of the reservoirs, and one or more SRU valves coupled to the output ports, to selectively couple an individual one of the fluid output ports to the heat exchanger. A pump and heat exchanger are located in serial fluid communication with the fluid output port. A controller is configured to selectively actuate individual SRU valves to couple the solvent/standard reservoirs to the heat exchanger, to actuate the pump, and to actuate the heat exchanger to maintain a sample of solvent/standard at a predetermined temperature for input into the analyzer. A return line is configured to return the solvent/standard sample to the reservoirs from the analyzer.

In yet another aspect of the invention, a sample handling apparatus includes an auto-sampling unit (ASU). The ASU includes one or more sample reservoirs configured to store one or more samples therein, and a sample port respectively coupled to each of the reservoirs. The sample reservoirs each have a sample transfer pathway coupled to the sample port and extending into the reservoir. The pathway has a plurality of orifices disposed at spaced locations along a length thereof. An actively controlled heat exchanger is located in series with the sample port, and one or more ASU valves are configured to selectively open and close a fluid flow path between the sample port and the heat exchanger. A controller is configured to selectively actuate the ASU valves to enable a sample to flow through the sample pathway to the heat exchanger, and to actuate the heat exchanger to maintain the sample at a predetermined temperature.

The features and advantages described herein are not all-inclusive and, in particular, many additional features and advantages will be apparent to one of ordinary skill in the art in view of the drawings, specification, and claims. Moreover, is should be noted that the language used in the specification has been principally selected for readability and instructional purposes, and not to limit the scope of the inventive subject matter.

In still another embodiment, a method of sample analysis includes disposing an actively controlled heat exchanger in upstream serial fluid communication with a sample analyzer, communicably coupling a controller to the heat exchanger, and disposing the heat exchanger in serial fluid communication downstream of at least one fluid handler selected from the group consisting of a stream selection unit (SSU), a solvent/standard recirculation unit (SRU), and an auto-sampling unit (ASU).

The SSU includes a plurality of stream input ports, a stream output port, and one or more SSU valves configured to selectively couple individual ones of the stream input ports to the stream output port. The controller is configured to selectively actuate the SSU valves to select and couple a stream source to the stream output port, and actuate the heat exchanger to maintain a sample of the stream source at a predetermined temperature.

The SRU includes one or more solvent/standard reservoirs, a fluid output port associated with each of the reservoirs, and one or more SRU valves coupled to the output ports, to selectively couple an individual one of the fluid output ports to the heat exchanger. The controller is configured to selectively actuate individual ones of the SRU valves to couple a reservoir to the heat exchanger, and to actuate the heat exchanger to maintain a sample of solvent/standard at a predetermined temperature for input into the analyzer. A return line is configured to return the solvent/standard sample to the reservoirs from the analyzer.

The ASU includes one or more sample reservoirs configured to store samples therein, and a sample port respectively coupled to each of the reservoirs. The sample reservoirs each have a sample transfer pathway coupled to the sample port and extending into the reservoir, the pathway having a plurality of orifices disposed at spaced locations along a length thereof. One or more ASU valves selectively couple the sample port to the heat exchanger. The controller is configured to selectively actuate the ASU valves to enable a sample to flow through the sample pathway to the heat exchanger, and to actuate the heat exchanger to maintain the sample at a predetermined temperature.

BRIEF DESCRIPTION OF THE DRAWINGS

The above and other features and advantages of this invention will be more readily apparent from a reading of the following detailed description of various aspects of the invention taken in conjunction with the accompanying drawings, in which:

FIG. 3 is a schematic, perspective view of another portion of an embodiment of the present invention;

FIGS. 5 and 6 are plan and top plan views, on an enlarged scale, of portions of the embodiment of FIG. 4;

FIG. 7 is a schematic, on an enlarged scale, of a portion of the embodiment of FIG. 4;

DETAILED DESCRIPTION

Figure 1A:
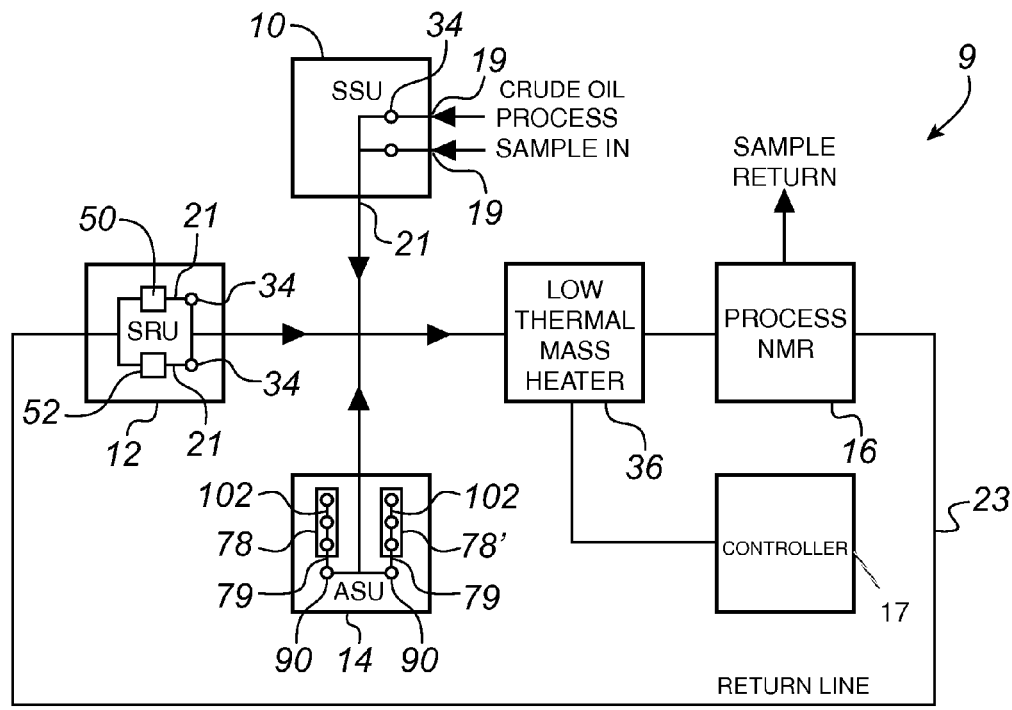
FIG. 1A is a schematic block diagram of a system in which exemplary embodiments of the present invention may be used.

In the following detailed description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. The following detailed description is, therefore, not to be taken in a limiting sense, and the scope of the present invention is defined by the appended claims and their equivalents. For clarity of exposition, like features shown in the accompanying drawings are indicated with like reference numerals and similar features as shown in alternate embodiments in the drawings are indicated with similar reference numerals.

Embodiments of the present invention include sampling devices that may be used alone or in combination with one another to provide consistently homogeneous samples to an analyzer such as an NMR analyzer (also referred to herein as a Magnetic Resonance Analyzer or MRA) in both online and offline applications. In various embodiments discussed herein, a suitable MRA includes the aforementioned D-Mash NMR analyzer from Qualion. Each of the various embodiments discussed hereinbelow deliver a fluid to the MRA at a predetermined set point temperature applicable for a particular application, while maintaining the set point temperature within a predetermined, relatively tight, tolerance. For example, a temperature of 40° C. might be selected for gasoline analysis, while FCC feed or crude oil samples generally are analyzed at 80° C.; in both of these examples, the temperature tolerance on sample flowing to the MRA is ±2.5° C. In should be recognized that although embodiments of the present invention are shown and described with respect to a nuclear magnetic resonance (NMR) spectroscopic analyzer, they may also be applied to other types of spectroscopic analysis, such as spectroscopy including infrared (IR), near-infrared (NIR), and Raman molecular spectroscopy Embodiments of these devices are presented in Sections A, B, and C below, in connection with the appended Figures, and include a stream selection unit/stream switching unit (SSU) 10, 10' (FIGS. 1A-1E), a Solvent (Sample) Recirculation Unit (SRU) 12, 12' (FIGS. 1A-1E, 2), and an Auto-Sampling Unit (ASU) 14, 14' (FIGS. 1A-1 E, 3, D. As described in greater detail below, representative embodiments of the SSU are used to receive and select between process samples arriving at the SSU (e.g., via conventional fast loops). By contrast, the ASU permits offline analysis of multiple samples through their injection into the MRA 16 (FIG. 1) from sample cylinders. The ASU may be useful as a vehicle for acquiring spectra of samples required for development of property model data sets, though it may be used for other purposes as well.

The ASU may be used in conjunction with the SSU when the MRA is online. Alternatively, the ASU may be used with the MRA in an offline mode without the SSU. Whether offline or online, a flowing sample at the analysis set point temperature may be desired to effect shimming (tuning) of the MRA magnet. For online implementations, a sample stream supplied through a fast loop may be used for this purpose. However, such sample streams generally have variable composition, which may lead to inconsistent shimming. Furthermore, it is well established in NMR spectroscopy that compounds having an NMR spectrum consisting of a single peak tend to provide the best results during shimming. Consequently, uncertainty of the shimming process may be compounded by the multiple peaks generally found in the typical process sample. In off-line mode, provision of such a stream has been difficult and generally impractical. Therefore, in embodiments of the present invention, the SRU may be used to circulate an appropriate, single-peak reference solvent through the MRA (e.g., through the MRA's flow-pipe probe) at the desired set point temperature.

For the MRA, water injected manually (i.e., at ambient temperature) into the flow-pipe probe at ambient temperature has been an established shim standard. However, it has also been the practice to further adjust (e.g., further shim) the MRA using a process stream (e.g., at the desired set point temperature) as described above, to optimize spectrometer performance following thermal equilibration at the analysis set point. Embodiments of the SRU are thus designed to facilitate shimming on water at analysis set point temperatures above ambient. However, because water is not compatible with hydrocarbon streams commonly analyzed with the MRA, the SRU can also deliver other process-compatible, (e.g., single-peak) standards to the MRA. Examples of these other standards include cyclohexane and ortho-xylene. Finally, in the case of heavy or dirty samples that may deposit residue inside the MRA (e.g., within the MRA's flow-pipe probe), the SRU may be used to deliver to the MRA flow-pipe probe an appropriate cleaning solvent, which may or may not be the same as the shim standard.

The SSU and SRU thus represent technologies that facilitate precise operation of, and spectral measurement by the MRA, while the ASU facilitates the rapid development of calibration sample data sets required for the development of property models. All three of these aspects tend to enhance precision in spectral measurement relative to prior approaches, through precise temperature control of materials delivered to the MRA for analysis. The ASU is particularly helpful in this regard because it helps to ensures the representative presentation to an analyzer of samples that may tend to stratify, separate, or otherwise become inhomogeneous over a relatively short time frame. Embodiments of the ASU thus permit offline measurement of spectra for a population of samples spanning the range of properties and chemistries characteristic of the process. Samples may thus be pre-collected (e.g., collected while the MRA is offline or otherwise unavailable), and may then be measured in a relatively short time frame following analyzer startup. Additionally, after the calibration data set has been developed and the analyzer is online and operational, the ASU may be employed to inject a 'standard' (check) sample, for verifying ongoing performance accuracy, and/or during system maintenance.

Referring now to the Figures, embodiments of the present invention will be more thoroughly described.

Turning now to FIGS. 1A-1D, various embodiments of the present invention are shown and described. One such embodiment is shown at 9 in FIG. 1A. In this embodiment, a system 9 includes an actively controlled heat exchanger 36 configured for being coupled in upstream serial fluid communication with a magnetic resonance analyzer 16. System 9 also includes a controller 17 communicably coupled to heat exchanger 36. Controller 17 may include substantially any microprocessor-based device such as a PC, PLC (Programmable Logic Controller), or other device commonly used for process automation. As also shown, heat exchanger 36 is disposed downstream of at least one fluid handler which may include a stream selection unit (SSU) 10, a solvent/standard recirculation unit (SRU) 12, and/or an auto-sampling unit (ASU) 14.

As shown, SSU includes a plurality of stream input ports 19, a stream output port 21, and one or more valves 34 configured to selectively couple individual ones of the stream input ports 19 to the stream output port 21. Controller 17 is configured to selectively actuate valves 34 to select and couple a stream source entering through ports 19 to output port 21, and to actuate the heat exchanger 36 to maintain a sample of the stream source at a predetermined temperature.

As also shown, SRU 12 includes one or more solvent/standard reservoirs 50, 52, a fluid output port 21 associated with each of the reservoirs, and one or more valves 34 coupled to the output ports, to selectively couple an individual one of the fluid output ports 21 to heat exchanger 36. Controller 17 is configured to selectively actuate the valves 34 to couple a reservoir 50, 52 to the heat exchanger 36, and to actuate heat exchanger 36 to maintain a sample of solvent/standard at a predetermined temperature for input into the analyzer 16. A return line 23 is configured to return the solvent/standard sample to the reservoirs from analyzer 16.

ASU 14 includes one or more sample reservoirs 78, 78' configured to store samples therein, and a sample port 79 respectively coupled thereto. Sample reservoirs 78, 78' each have a sample transfer pathway 102 coupled to the sample port and extending into the reservoir, the pathway having a plurality of orifices 104 disposed at spaced locations along a length thereof. One or more ASU valves 90 selectively couple the sample ports 79 to heat exchanger 36. Controller 17 is configured to selectively actuate the ASU valves 90 to enable a sample to flow through sample pathway 102 to the heat exchanger, and to actuate the heat exchanger to maintain the sample at a predetermined temperature. Various aspects of this system 9 will be discussed in greater detail hereinbelow.

Figure 1B:
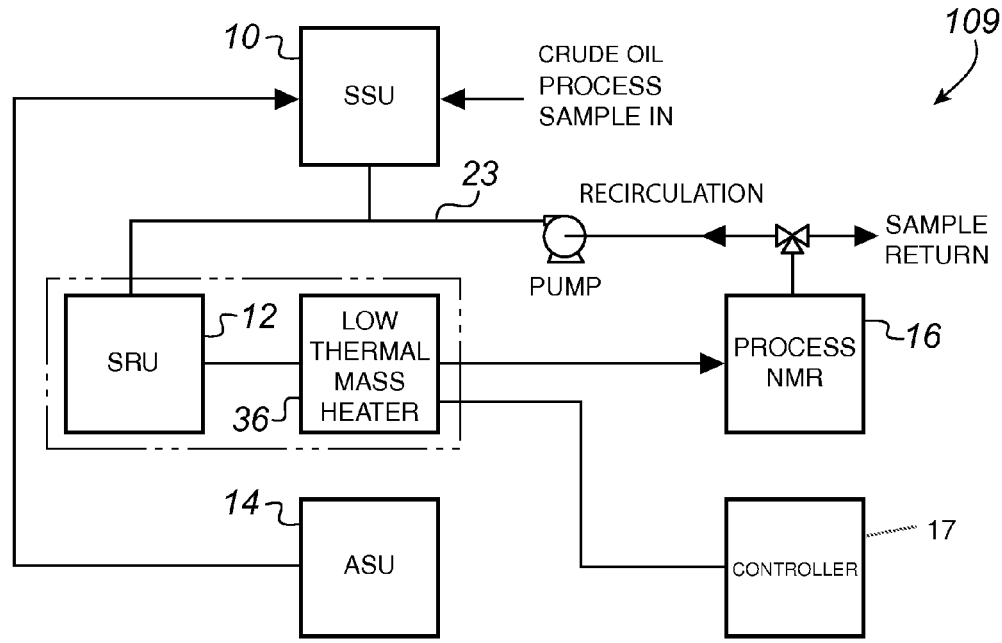
FIGS. 1B-1D are schematic block diagrams of variations of the system of FIG. 1A.
Figure 1C:
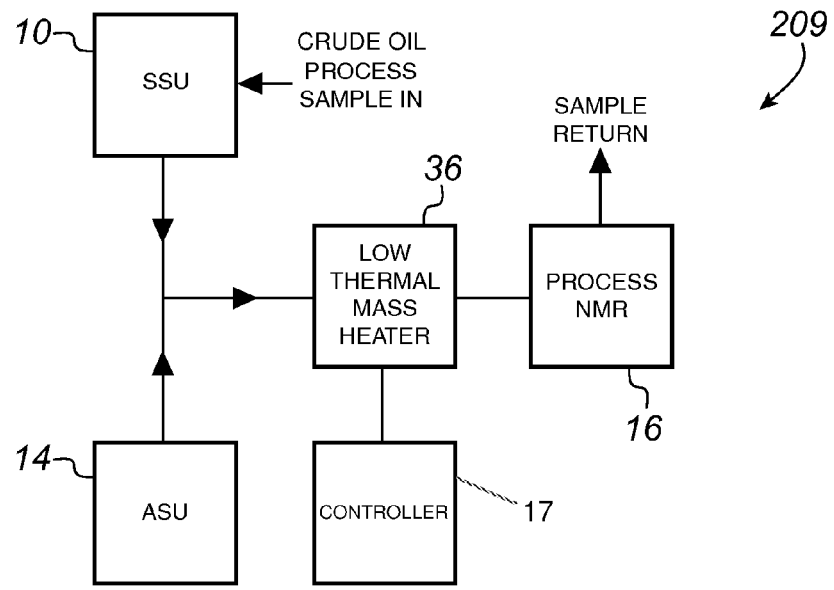
Figure 1D:
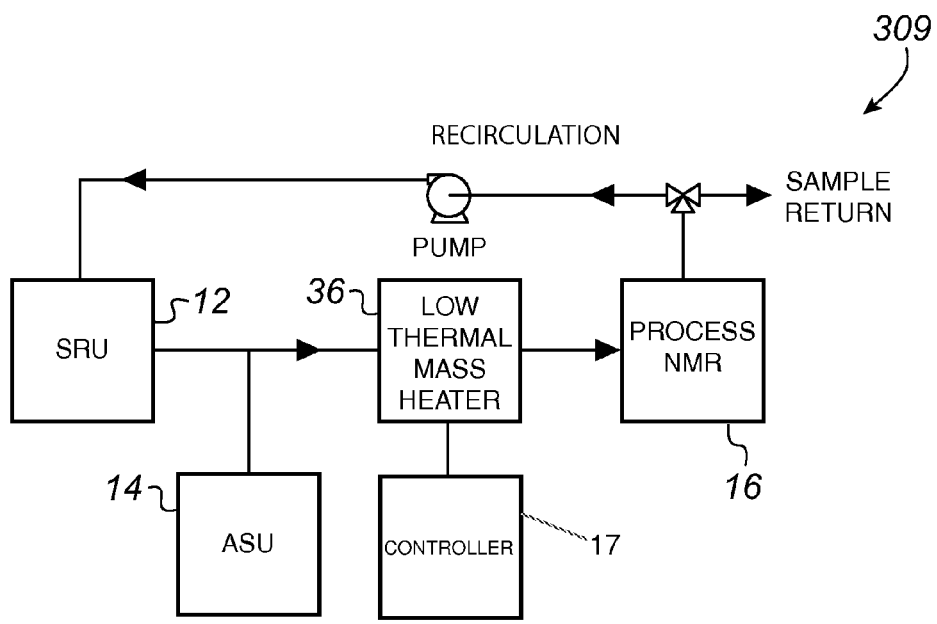

Referring now to FIGS. 1B-1D, particular variations of system 9 are shown as systems 109, 209, and 309. System 109 includes an exemplary fluid flow configuration in which ASU 14 is disposed upstream of SSU 10, which in turn, is disposed upstream of SRU 12. Sample or solvent/standard streams are then passed from SRU 12 to heat exchanger 36. In FIG. 1C, system 209 includes only two of the aforementioned fluid handler types, namely, an SSU 10 and an ASU 14 disposed upstream of heat exchanger 36. In FIG. 1D, system 309 also uses only two of the fluid handler types: an SRU 12 and an ASU 14.

It should be recognized that the foregoing configurations are merely exemplary, and that the various fluid handlers (SSU, SRU, and ASU) described herein, may be used alone or in nominally any combination, along with heat exchanger 36 and processor 17, to supply fluid to an analyzer 16 in accordance with the present invention. Various additional, optional aspects of the present invention will now be described in greater detail.

A. Stream Switching Unit (SSU)

Figure 1E:
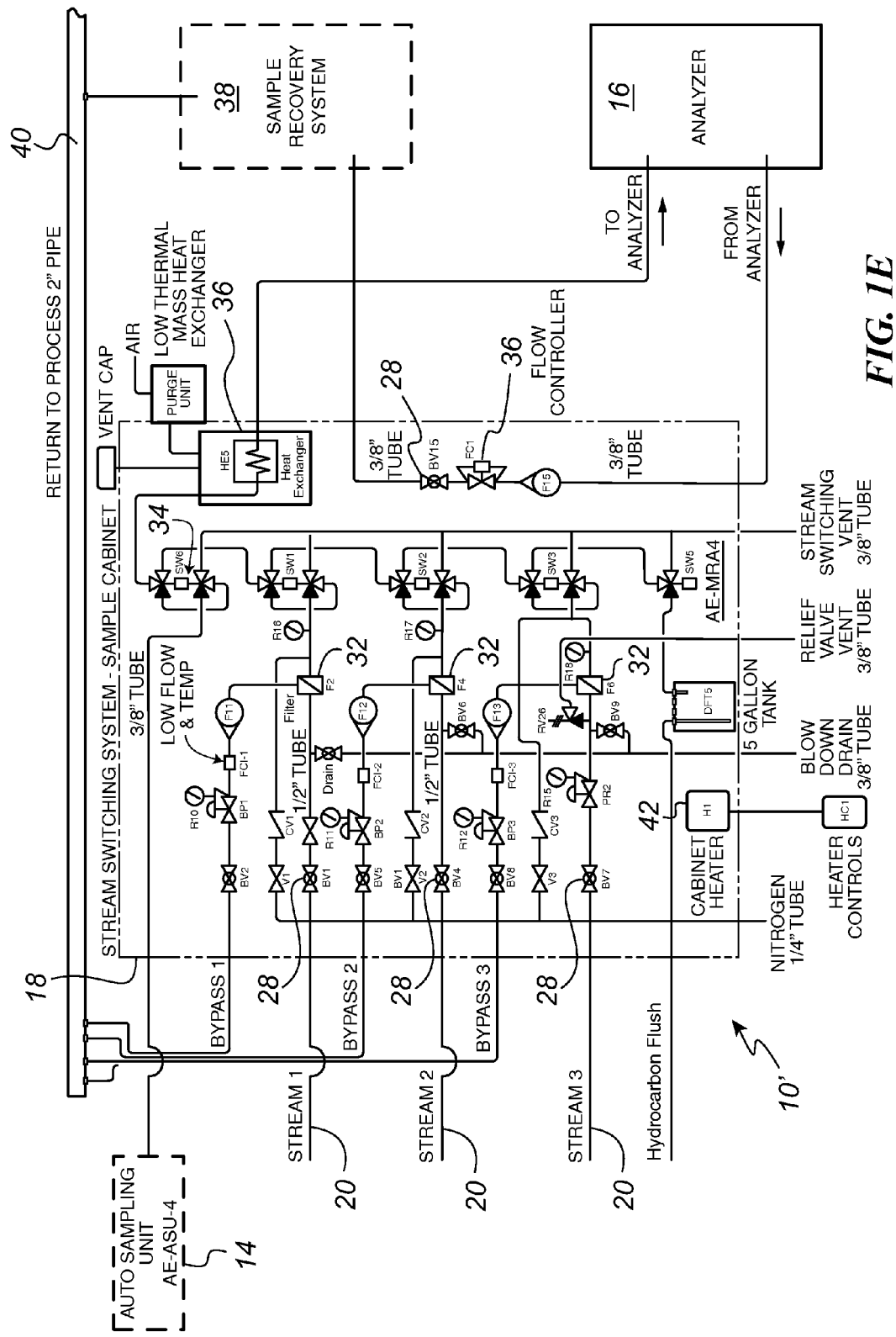
FIG. 1E is a schematic view of a portion of an embodiment of the present invention.

Referring to FIG. 1E, an embodiment of the Stream Switching Unit (SSU), shown at 10' is configured to permit online analysis of refinery streams ranging from gasoline, gasoline blendstocks, and light distillates to heavy hydrocarbons such as crude oil, vacuum gasoil, or FCC feed. It sequentially selects between fast loops carrying sample, and thermally conditions each to meet the temperature specification of the MRA prior to analysis.

1. Design and Operation.

In the particular embodiment shown, SSU 10' is integrated into a cabinet 18, and is configured to select and thermally condition the sample before delivery to the MRA 16. Upon entering the SSU 10', fast flow inputs 20 pass through flow meters 28 (and/or flow controllers, not shown), which maintain consistent flow, and through a self-cleaning 'T' filter 32. Sample may also, optionally, be inputted into SSU 10' by ASU 14 as shown in phantom. Sample drawn from the fast loop through the filter 32, or from optional ASU 14, passes through double block and bleed valves 34 (e.g., in multi-stream embodiments, as shown) for stream selection, which is then passed through an actively controlled, (e.g., direct contact, low thermal mass) heat exchanger 36 (discussed hereinbelow) prior to delivery to MRA 16. After being analyzed by the MRA, the fluid is passed to a flow meter 28 and flow controller 36 integrated into the SSU 10', to help maintain consistent flow. This spent sample exiting the MRA 16 may then be sent to an optional sample recovery system 38 (shown in phantom) and/or back to the process, such as via Return 40.

2. Temperature Control.

In a representative embodiments, the temperature of sample arriving at the SSU from the fast loop $(T_{fl})$ falls within a range between set point $(T_s)$ plus zero ° C. and minus 30° C. $(T_{fl}=T_s+0°$ C. to $T_s-30°$ C.). Thus, for example, crude oil to be analyzed at a nominal temperature of 80° C. must arrive at the SSU between 50° C. and 80° C. (155° F. and 175° F.). Sample in the fast loop has a predetermined nominal flow rate, which in this particular example, is about 3.8 L/min. (For purposes of discussion here and in other sections below, the sample analysis temperature will be taken to be 80° C., although higher or lower temperatures may be used as appropriate.)

Temperature control inside the cabinet is achieved by means of a dedicated heater 42, which maintains the cabinet internally at the desired set point, e.g., 80° C. (175° F.) to help minimize any temperature losses of the sample fast loop flow. A suitable actively controlled, (e.g., direct contact and low-thermal-mass) heat exchanger 36, is model No. 1-57-76-1 (240 volts, 1850 watts) available from Watlow- Hannibal (An operating unit of Watlow Mo.) of Hannibal Mo., ("Watlow") which performs final thermal "polishing" to ensure that the selected sample stream flowing to the MRA is within the predetermined temperature tolerance (e.g., of ±2.5° C. in particular embodiments). In this embodiment, the actively controlled, direct contact heat exchanger provides a heating element in direct contact with the sample stream, rather than with another fluid. This direct contact, in combination with the active, thermostatic temperature control, and configuration of the fluid handlers as described herein, provides relatively rapid temperature response over a relatively wide range of temperatures, at relatively high flow rates. For example, the nominal flow rate of the heat exchanger 36 is 1 L/min. At this flow rate, the temperature recovery time associated with switching between streams at 50° C. and 80° C. is less than 8 seconds, or, in particular embodiments, approximately 5 seconds, or less, which is short enough to avoid disrupting the thermal equilibrium of the MRA flow-pipe probe and related hardware. Moreover, this configuration permits various streams, at various distinct input temperatures, to be successfully selected and their temperatures "polished", to enter the MRA at the predetermined temperatures.

3. It should be recognized that although actively controlled, direct contact heat exchangers have been shown and described herein with respect to particular embodiments, substantially any actively controlled heat exchangers (heaters), capable of providing the desired temperature response and temperature range, at desired sample flow rates, may be used without departing from the scope of the invention. For example, conventional coil and cable heaters, flexible heaters, radiant heaters, etc., such as available from Watlow, may be applied to a sample pathway, and/or within close proximity thereto, to heat the sample without being in direct contact with the fluid sample. Other indirect heating approaches, including induction and/or microwave heaters, may also be used. Conventional tubular or shell and tube heat exchangers, including spiral tube and/or plate and frame heat exchangers, e.g., which provide a thermal mass (including a thermal exchange fluid) less than that of the fluid in the sample path thereof, may be usable in various embodiments of the present invention. In such heat exchangers, sample may flow in the same, or opposite, direction as a thermal exchange fluid, such as through adjacent (e.g., coiled), tubes, or along opposite sides of a plate.

Input for System Flush/Clean and MRA Shimming.

For crude oil applications, a minimum of one light stream such as diesel or kerosene may be provided in addition to the crude sample fast loop to permit periodic cleaning of the flow-pipe probe in the MRA and lines leading to it. This same stream, or any such process stream, may be used in the aforementioned shimming process.

B. Solvent (Sample) Recirculation Unit (SRU)

Figure 2:
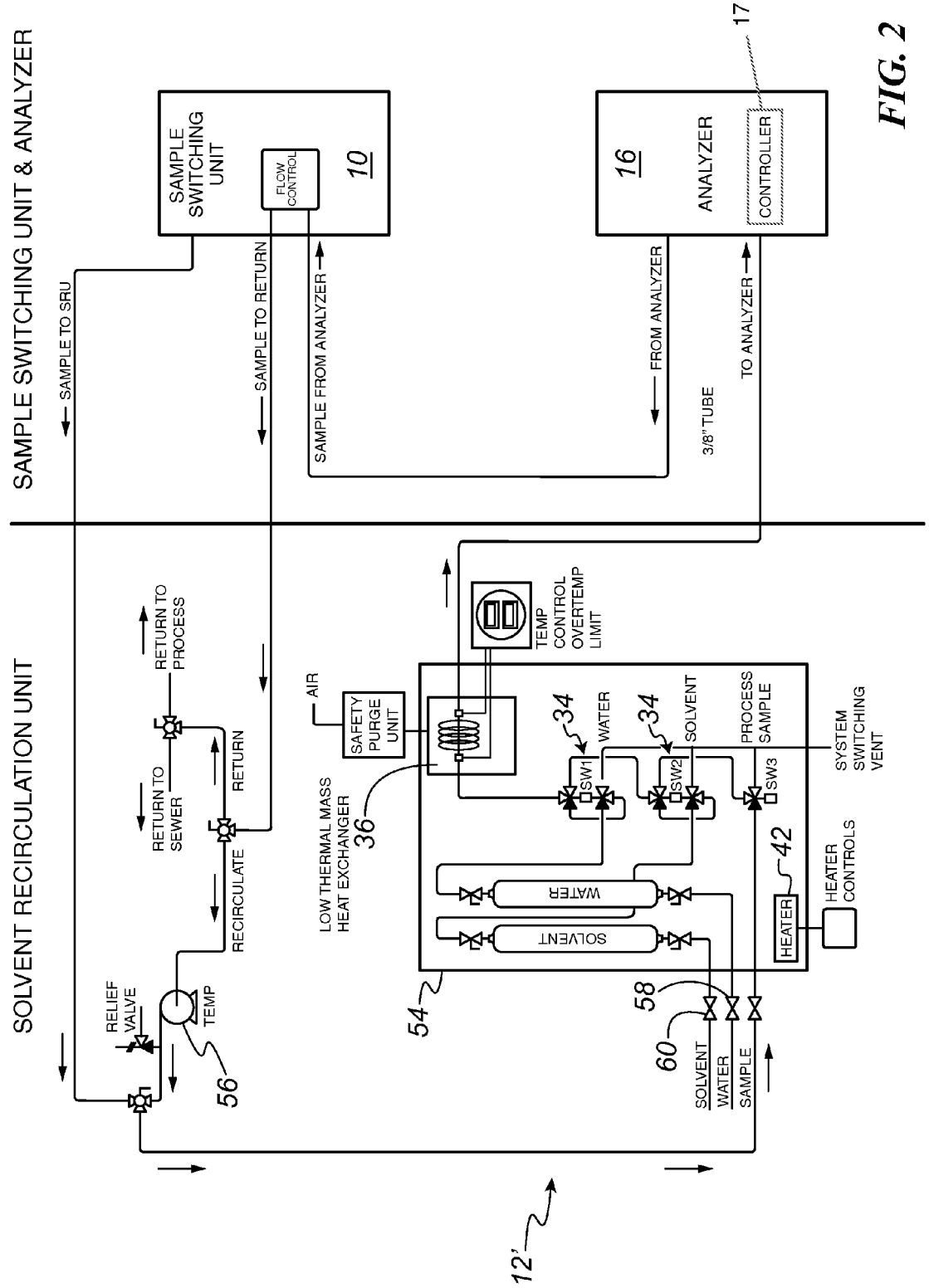
FIG. 2 is a schematic view of another portion of an embodiment of the present invention.

Referring to FIG. 2, embodiments of SRU 12, 12' are configured to thermally condition either a process sample or standard/solvent in a reservoir during closed-loop recirculation (via return line 23) to the MRA 16. An objective of the SRU is to supply the MRA 16 with a shim/calibration material (e.g., water, via cylinder 50 as shown, or optionally, some other reference material such as cyclohexane, whose NMR spectrum, like water, preferably exhibits a single peak) for shimming the magnet of the MRA 16 as discussed hereinabove. This is accomplished while maintaining temperature and flow at levels nominally matching those of sample arriving from the SSU 10, 10'. Additionally, the SRU 12' may be used to provide pre-heated solvent, via cylinder 52, to the MRA 16 to clean its flow-pipe probe, and/or for use as a secondary shim/calibration material, as discussed in greater detail hereinbelow.

1. Design and Operation.

In the embodiment shown, SRU 12' includes a cabinet 54 with a cabinet heater 42 (e.g., as used in the SSU 10'), one or more insulated and heat-jacketed cylinders or canisters 50, 52 (e.g., fabricated from aluminum or other suitable material to facilitate heat transfer); a low-thermal-mass, actively controlled, (e.g., direct contact) heat exchanger 36 (e.g., as used in the SSU 10'); and a recirculation pump 56 disposed either within cabinet 54 or outside the cabinet as shown. Appropriate utility connections (not shown) supply needed electrical power and/or air to actuate valves 34 used to selectively couple the flow from canisters 50, 52 to heat exchanger 36. Additionally, water and shim/cleaning solvent supplies (the latter, for example, being under nitrogen pressure) are respectively connected to inputs 58, 60, for filling the canisters. Provision may be is made, e.g., in the form of pressure relief valves (not shown) to accommodate expansion of the fluid upon heating from ambient to the set point.

Prior to shimming/calibration, a procedure may be implemented by which alternate "shots" of pre-heated nitrogen and solvent are delivered through the system to displace fluid (e.g., previously analyzed sample material) from the transfer lines and MRA 16. Nitrogen used for this purpose would flow through suitable lines inside SRU 12'.

In operation, canister 52 is provided with a solvent that is compatible with the particular process fluid to be analyzed by MRA 16. (The solvent may also be used for shimming, as described below.) Due to the high efficiency of the actively controlled heat exchanger 36 as used in this exemplary embodiment, for an analysis set point of, e.g., 80° C., solvent (or water) may enter the heat exchanger 36 as low as about 50° C., to reduce the requirement to preheat and maintain a quantity of solvent (or water) at 80° C. within canisters 50, 52.

In particular embodiments, valves 34 may be operated to provide water from canister 50 at the desired temperature (at e.g. 80° C.), for shimming the MRA 16, followed by a second shimming operation using the solvent in canister 52, also at the desired temperature. In particular embodiments, the solvent may be cyclohexane, toluene, or ortho-xylene, which also serves as a process-compatible reference (standard) that can be used frequently to demonstrate the repeatability of spectral measurement (i.e., the stability of the MRA's spectral response).

This approach eliminates the variations due to temperature differences experienced during conventional two-step shimming operations, in which water at ambient temperature is provided for the first shimming operation, followed by a second shimming operation using a temperature-controlled process stream, e.g. at 80° C., to compensate for any changes in the spectrometer response, such as may attend the temperature change. Moreover, embodiments of the present invention may be used to advantageously eliminate the need for a two-step shimming operation, by eliminating the need for shimming with water. Instead, MRA 16 may simply be shimmed using cyclohexane or some other reference/standard (e.g., at the desired process temperature) whose NMR spectrum, like water, exhibits a single peak. In this regard, however, it should be recognized that although reference/standards exhibiting a single peak may be desired in many applications, materials exhibiting multiple peaks may also be used for shimming in other applications.

2. Temperature Control.

Embodiments of SRU 12' are capable of maintaining temperatures at predetermined levels, e.g., between 40° C. and 100° C. Lower temperatures may be appropriate for lighter hydrocarbon samples such as gasoline, while crude oil is preferably analyzed at 80° C. to prevent waxing. Still higher temperatures may be required for heavier materials such as vacuum gasoil. Cylinders made of aluminum rather than stainless steel, if suitable for prolonged contact with the particular fluid used, at the particular temperatures concerned, may be used to improve heat transfer to the solvent, as mentioned above.

3. Offline or Online Use.

The SRU may be used alone, or in conjunction with either the ASU 14, 14' or the SSU 10 as shown. Moreover, when used with SSU 10, hybrid approaches may be used, such as for online applications in which the SRU 12' may be used without running the solvent/sample supply through the SSU prior to analysis, but is otherwise controlled by controller 17, such as may be integrated with the MRA 16. In such a configuration, solvent may be re-circulated back to SRU 12' via SSU 10 as shown, or may be discarded after use by the MRA 16, e.g., for recycling.

For offline projects, samples may be injected directly into the MRA 16 from the ASU 14' (as discussed hereinbelow), while the SRU interfaces separately to the MRA 16, for solvent supply.

C. Auto-Sampling Unit (ASU)

Figure 3:
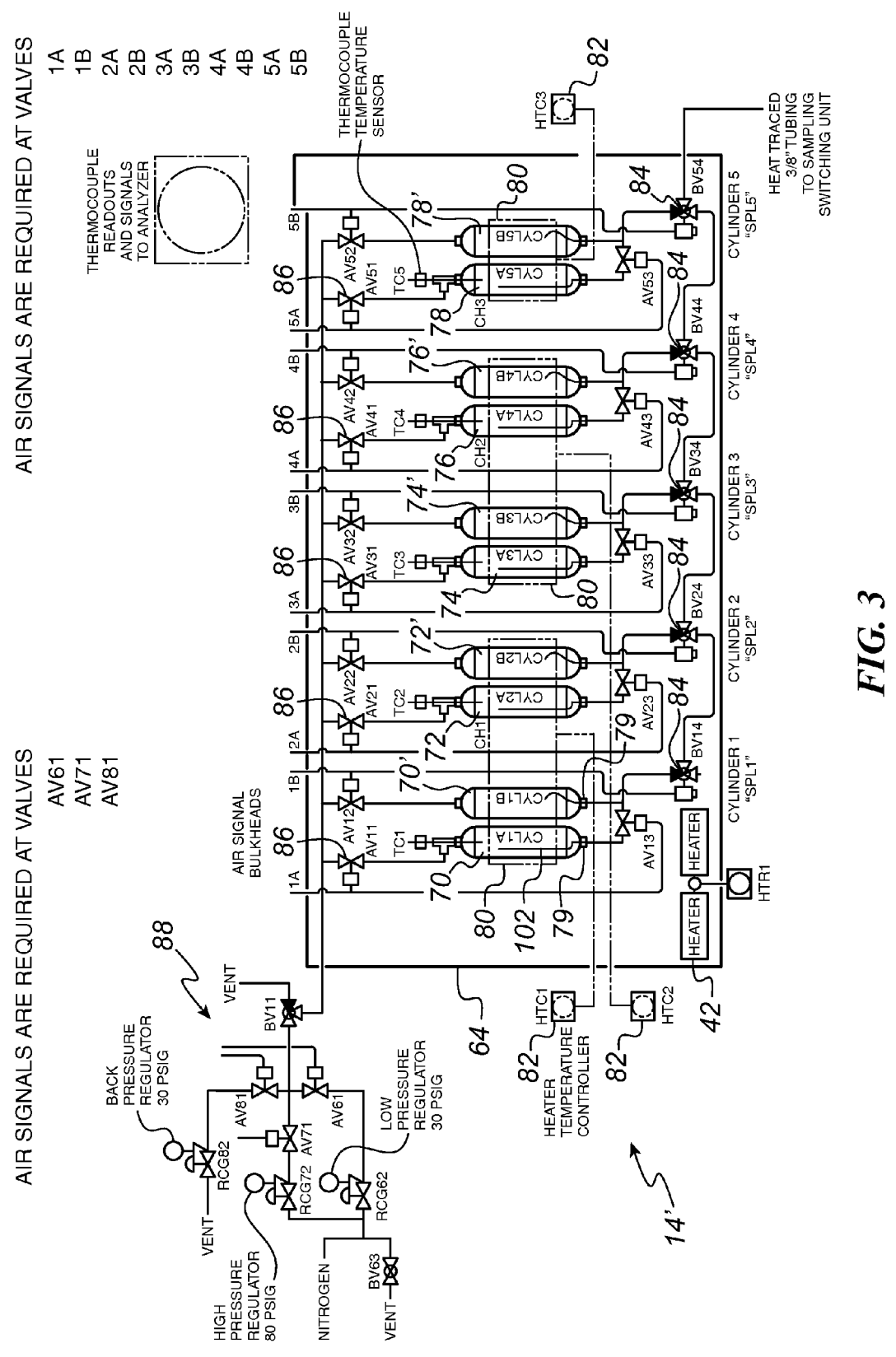

Referring now to FIG. 3, a more detailed, representative embodiment of an ASU in accordance with the present invention is shown at 14'. As discussed above, the various embodiments of the ASU may be operated with the MRA 16 independently or in combination with SSU 10, 10' or SRU 12, 12'. In the embodiment shown, ASU 14' may be used to preheat multiple samples (e.g., up to five samples as shown) contained in separate cylinders 70, 72, 74, 76 and 78, respectively, to facilitate automatic acquisition of sample spectra for simplified, reliable model development or validation. (Optional secondary cylinders 70', 72', 74', 76' and 78', as shown in phantom, will be discussed in greater detail hereinbelow, with reference to FIG. 4.)

1. Temperature Control and Operation.

In particular embodiments, the ASU 14' includes a heated cabinet 64 (e.g., heated by one or more cabinet heaters 42) and sample cylinder heaters 80 to thermally condition samples at temperatures from 40° C. to 80° C. (104° F. to 175° F.). In the example shown, five two-liter sample cylinders A are close-coupled to sample cylinder heaters 80 to promote efficient heat transfer, to minimize the time required to achieve the desired temperature. (The heaters 80 may be in the form of a suitable heating blanket, which is then covered by a jacket providing thermal insulation. Temperature controllers 82, in conjunction with thermocouples or other temperature sensors 106 (FIG. 7) may be used to monitor the surface temperature of the heater, the cylinder, and the cylinder contents.)

In preliminary tests, examples of ASU 14' provided a heating rate of approximately 1° C. per minute, so that samples were heated from ambient to 80° C. in approximately one hour. By contrast, calculations suggested that heating the same sample in unclad cylinders could take 48 hours if accomplished solely by means of maintaining the atmosphere in the cabinet at 80° C. A controller 82, that monitors the temperature of the heaters 80, the cylinders, and the sample, may also control electrical power to the heaters 80, to provide an initial, high heating rate, followed by diminished thermal input as sample approaches the set point temperature. Moreover, a fast-response, low thermal-mass sample heater, such as heat exchanger 36 used with SSU 10' and SRU 12' discussed above, may be used to reduce (e.g., from 80° C. to 50° C. or less) the requirement for sample preheating.

As also shown, a series of three way valves 84 are coupled to the bottom of each cylinder 70, 72, etc., to control and direct the flow of sample within the ASU and output therefrom (e.g., to the MRA 16, optionally via SSU 10'. Valves 86 at the tops of the cylinders control the supply of gas (e.g., nitrogen, instrument air or helium) from a gas supply 88, used to displace samples from the cylinders for subsequent analysis by the MRA 16. External connections are provided for coupling to the gas supply 88 (e.g., of at least about 80 psi) and electrical power for the heaters 42, 80. The system may be closely coupled to the MRA 16 to minimize the length of the (e.g., heat traced) tubing therebetween, and to help maintain a constant flow of temperature-controlled sample.

2. Option for Crude Mixing

Figure 4:
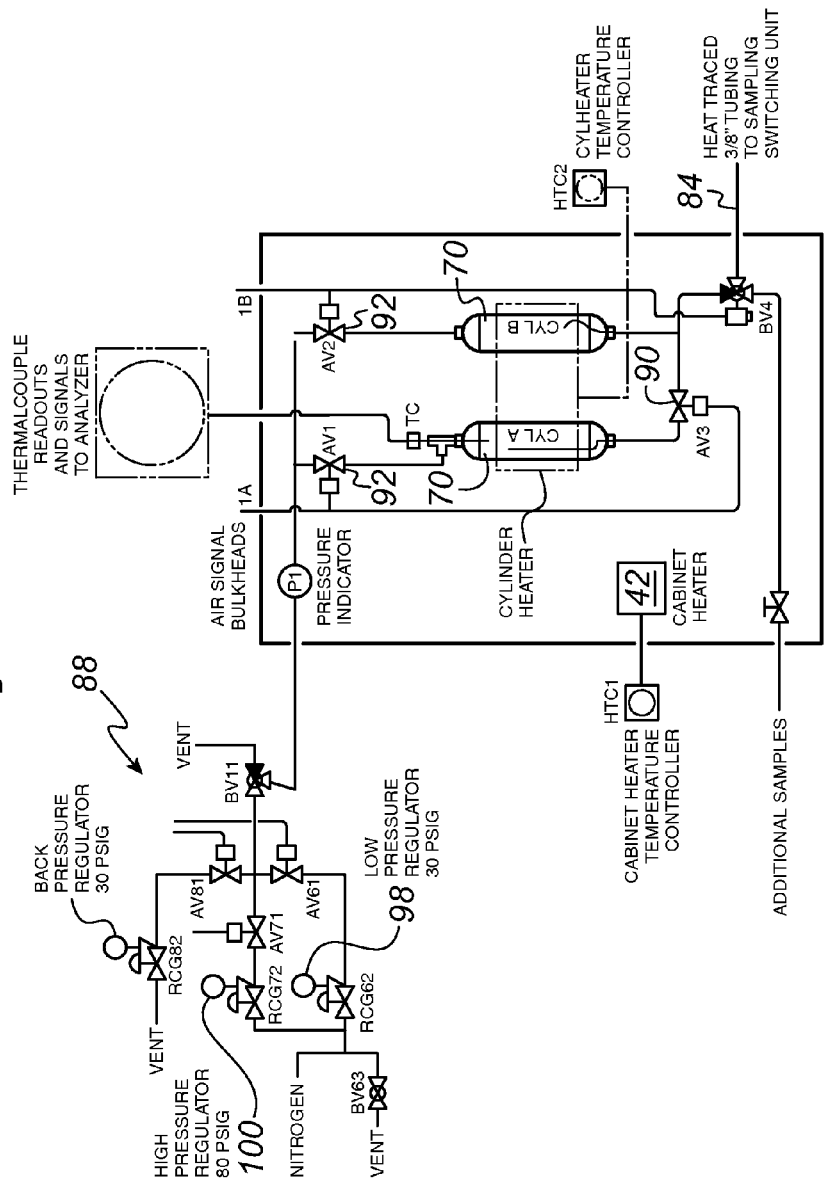
FIG. 4 is a schematic view, on an enlarged scale, of a portion of the embodiment of FIG. 3.

As mentioned hereinabove, at elevated temperature where viscosity is reduced, non-homogeneous materials such as crude oil and the like have a tendency to stratify during the time required for thermal equilibration. Therefore, in applications involving these materials, it may be desirable to provide ASU 14' with the ability to homogenize these materials prior to injection into the MRA 16. As best shown in FIG. 4, an optional variation of ASU 14' is described, which effectively mixes crude oil or other non-homogeneous samples that may otherwise tend to separate/stratify during thermal conditioning prior to analysis, in order to homogenize the crude oil or other non-homogeneous samples.

a. Cyclone Mixer.

In this embodiment, the size of the cabinet 64 (FIG. 3) is increased to accommodate the pairing of additional cylinders 70', 72', etc., with sample cylinders 70, 72, etc., respectively. One representative pairing is shown and described as 70, 70' (or cylinders A & B) in FIG. 4. Oriented vertically, the cylinders are connected to each other by means of tubing and valves 90 at the bottom; while valves 92 at the top permit either the delivery of a suitable gas (e.g., nitrogen, instrument air, or helium) from supply 88 (FIG. 3) for pressurization, or the venting of gas to relieve pressure.

Displacement Mixing.

With reference to FIGS. 4-6, mixing may be accomplished by pressurizing cylinder A (70) using gas from gas supply 88, and opening the valve 90 to permit displacement of sample into cylinder B (70'). As best shown in FIGS. 5 & 6, a sample inlet tube 94 is provided to deliver sample to the interior of cylinder B (70'). A proximal end of tube 94 is fastened to the cylinder inlet. The tube extends from the proximal end toward the distal end, generally curving radially outward towards the periphery of the cylinder. In particular embodiments, the curvature is configured so that the distal end of tube 94 is substantially tangent to the inside surface of the cylinder on a plane substantially perpendicular to the cylinder axis, approximately 10-50 percent of the distance from the bottom to the top of the cylinder as shown. As a result, sample entering cylinder B (70') does so in a direction substantially perpendicular to the cylinder axis and flows along the inside surface of the cylinder, creating a radial flow facilitating the mixing of sample.

Prior to injection, Cylinder B may be purged with an appropriate, dry gas, e.g., from gas supply 88 (FIG. 4). Helium may be preferred for some applications, as some processes are sensitive to nitrogen or oxygen; and since helium is substantially insoluble in liquids, its use tends to eliminate off-gassing and the formation of bubbles upon reduction of sample pressure, which might otherwise occur in the event a more soluble gas were used for the same purpose.

As sample fills cylinder B (70'), it compresses the gas therein (since valve 92 has been closed). (Depending on the pressure applied to Cylinder A (70), a pressure relief valve (not shown) may or may not be required to permit venting of the gas through the valve 92 at the top of the cylinder 70' and to facilitate the aforementioned displacement of sample into Cylinder B (70') through the tube 94.) Because materials such as crude oil contain volatile components that boil below 80° C. at ambient pressure, adequate pressure must be maintained to prevent boiling/distillation of these components during filling of cylinder B (70'). Additionally, the initial flow rate should be relatively slow until the distal end of the inlet tube is submerged so as to minimize the distribution of sample on the inside surface of the cylinder above the level of the sample. To accomplish this, gas supply 88 may use dual-regulators, e.g., including both low and high pressure regulators 98 & 100, respectively, to apply low pressure initially, and subsequently provide higher gas pressure to produce higher flow rates as may be desired to facilitate mixing and to overcome pressure build-up within cylinder B (70').

Since sample initially filling cylinder B (70') may not be representative of the bulk sample in cylinder A (70), the inlet tube 94 may be provided with a relatively small hole 96 (FIG. 5) near its proximal end just inside the cylinder to facilitate upward displacement of sample that may otherwise collect at the bottom of cylinder B (e.g., below the distal end of the inlet tube 94). The geometry of the distal end of the inlet tube 94 may also be formed as desired, such as in the form of a nozzle, to increase the velocity of sample entering cylinder B therefrom, and to create back-pressure sufficient to promote desired levels of flow through the hole 96.

Displacement/Delivery to the MRA.

Once sufficient mixing has taken place in cylinder B (70'), valve 90 may be closed, and valve 84 associated with the particular cylinder pair 70, 70' may be opened to allow displacement of sample from cylinder B into the MRA 16 (e.g., either directly, or via SSU 10'). In this regard, gas pressure is applied through valve 92 to drive the sample back out through the inlet tube 94.

b. Distributed Sampling During Sample Displacement.

Turning now to FIG. 7, as a further alternative embodiment, a cylinder A (shown as 170) may be provided with a tube 102 attached to its lower outlet. The tube is generally long enough to extend along at least 50 percent or more of the length of the cylinder, and in particular embodiments, at least part way into the tapered end to help limit any lateral movement of the tube 102. A plurality of holes (orifices) 104 are spaced along the length of the tube 102 to permit sample to flow into the tube 102 from multiple levels in cylinder A (170), i.e. to facilitate "distributed sampling." The spacing and/or diameter of the holes 104 may be varied from bottom to top to help maintain the flow rate of sample displaced through each hole nominally constant, e.g., regardless of the total amount of sample remaining in the cylinder. As in the case of the sample inlet tube 94 in cylinder B, a hole 96 may be provided at the base of tube 102 to help ensure that sample is displaced in a quantitative and representative fashion. Cylinder 170 may be provided with a temperature sensor, such as a thermocouple 106 as shown.

c. Flow-Through Cyclone Mixing Chamber.

Figure 8:
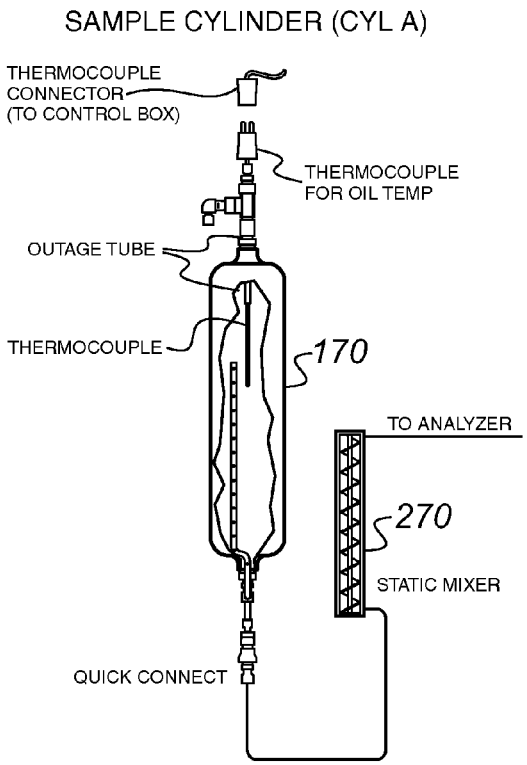
FIG. 8 is a schematic view of yet another embodiment of the portions shown in FIG. 4.

Referring to FIG. 8, it is expected that in many applications, the aforementioned distributed sampling provided by the use of tube 102, may provide sample whose composition remains substantially constant as the cylinder 170 is drained. In such applications, it may not be necessary to subsequently send the sample into a cylinder B (70', 170) for subsequent mixing as described above, but rather, the sample may be injected directly from cylinder A (70) into the MRA 16 (or SSU 10').

Alternatively, rather than quantitatively displace all the contents of cylinder A into cylinder B, and then from cylinder B to the MRA 16, a smaller receiving cylinder B' may instead function as a flow-through mixing chamber 270. With a volume of about 10%-25% that of cylinder A (70), sample displaced continuously from cylinder A would fill B' and dynamically mix within B' en route to the MRA 16 (or SSU 10'). A curved inlet tube 94 such as described above with respect to cylinder B (70'), or lengthened as shown at 94' to extend helically along substantially the length of cylinder 270, may be provided. Tube 94, 94' may also be used in combination with a perforated drain tube 102 as described above with respect to FIG. 7 (but inverted, so that sample exits from the top), to facilitate the quantitative filling of B' while A is emptied.

Figure 9:
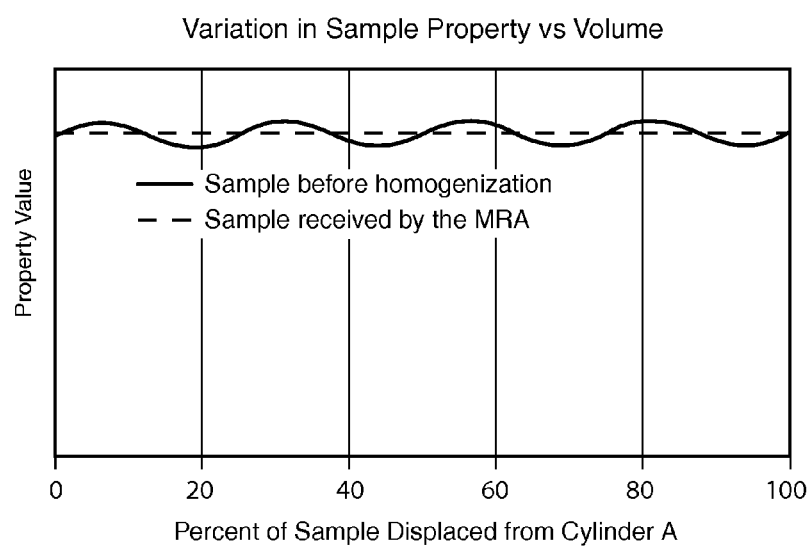
FIG. 9 is graphical representation comparing sample before and after being processed by embodiments of the present invention.

The volume of B' would be sized appropriately to dampen the magnitude of the transient inhomogeneity experienced while draining the contents of A. For this approach, transient inhomogeneity in many applications should average to constant composition across the, e.g., 2-liter volume drained from A, i.e. a line regressed through a plot of composition versus drained volume should have a slope approximately equal to zero, as shown in FIG. 9. In practice, it may be desirable to fill B' (270) from the bottom, and the sample would be allowed initially to exit through the top to displace gas being closed.

3. Alternative Uses of the ASU.

It is contemplated that embodiments of the ASU 14, 14' will be used primarily as an aid for building and validating a property model as discussed hereinabove, i.e., it permits offline measurement of spectra for a population of samples spanning the range of properties and chemistries characteristic of the process. Samples collected while the MRA is offline, e.g., before installation of the MRA 16, may be measured in a relatively short time frame following MRA startup. Additionally, after the calibration data set has been developed and the MRA is online and operational, the ASU may be employed to inject a 'standard' (check) sample (e.g., via SSU 10') for ongoing performance verification or during system maintenance. Finally, in the case of heavy or dirty samples that may deposit residue inside the MRA 16, the ASU may be used to flush the analyzer system with an appropriate cleaning solvent.

It should be understood that any of the features described with respect to one of the embodiments described herein may be similarly applied to any of the other embodiments described herein without departing from the scope of the present invention.

In the preceding specification, the invention has been described with reference to specific exemplary embodiments for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

Having thus described the invention, what is claimed is:

1. A system configured for delivering and analyzing crude oil comprising:

a spectroscopic analyzer that detects compositional properties of crude oil;

a conduit that allows fluid communication with the spectroscopic analyzer, the conduit being configured for receiving the crude oil from a source of crude oil and configured for delivering the crude oil into the spectroscopic analyzer;

a heat exchanger in thermal communication with an interior of the conduit that exchanges heat with the crude oil when the crude oil is in the conduit; and a controller configured to actuate the heat exchanger in order to maintain crude oil that is entering the spectroscopic analyzer from the conduit at a set point temperature.

2. A system as set forth in claim 1 further comprising a homogenizer in fluid communication with the conduit that is configured for receiving crude oil and homogenizing the crude oil prior to the crude oil entering the spectroscopic analyzer.

3. A system as set forth in claim 2 wherein the heat exchanger is in thermal communication with the homogenizer.

4. A system as set forth in claim 3 further comprising a temperature sensor located in the homogenizer, where the temperature sensor is in communication with the controller while detecting the temperature of crude oil in the homogenizer.

5. A system as set forth in claim 1 wherein the heat exchanger is disposed in the conduit in order to be in contact with the crude oil when the crude oil is carried by the conduit.

6. A system as set forth in claim 5 wherein the controller and heat exchanger are configured to control and maintain the temperature of the crude oil to within plus or minus 2.5° C.

7. A system as set forth in claim 1 further comprising a temperature sensor that is located within a path of crude oil when the crude oil is flowing through the system.

8. A system as set forth in claim 7 wherein the temperature sensor is located in the conduit.

9. A method of delivering crude oil from an online crude oil processing stream into a spectral analyzer, the method comprising:

diverting crude oil from the online processing stream with a stream selection unit (SSU);

automatically measuring the temperature of the diverted crude oil, with a temperature sensor and generating a signal representative of the measured temperature;

comparing the measured temperature of the diverted crude oil with a previously electronically stored set point temperature using a controller that is programmed in order to receive the signal representative of the measured temperature of the crude oil and compare the measured temperature with the stored set point temperature;

controlling with a controller, a heat exchanger that is in thermal communication with the diverted crude oil, in order to maintain the diverted crude oil at the set point temperature;

delivering the diverted crude oil that is maintained at the set point temperature into a spectroscopic analyzer by making use of a conduit that allows fluid communication with the spectroscopic analyzer; and automatically analyzing the diverted crude oil that is maintained at the set point temperature with the spectroscopic analyzer.

10. The method as set forth in claim 9 further comprising automatically homogenizing the diverted crude oil with a mixer prior to delivering the diverted crude oil into the spectroscopic analyzer.

11. The method as set forth in claim 9 wherein controlling the heat exchanger comprises placing the diverted crude oil into contact with the heat exchanger.

12. The method as set forth in claim 11 wherein controlling the heat exchanger further comprises controlling the heat exchanger in order to maintain the temperature of the diverted crude oil to within plus or minus 2.5° C. of the set point temperature.

13. The method as set forth in claim 9 further comprising passing diverted crude oil over a temperature sensor that is located in the path of the diverted crude oil.

14. The method as set forth in claim 13 wherein controlling the heat exchanger comprises using temperature readings from the temperature sensor in order to control the heat exchanger.

* * * * *